(12) United States Patent
Romanoschi et al.

(10) Patent No.: US 11,154,495 B2
(45) Date of Patent: Oct. 26, 2021

(54) MULTICOMPONENT GUMMY COMPOSITIONS WITH SOFT CORE

(71) Applicant: Church & Dwight Co., Inc., Princeton, NJ (US)

(72) Inventors: Ovidiu Romanoschi, Highland Park, NJ (US); Caryn Oryniak, Hillsborough, NJ (US); Luis Muniz, Brooklyn, NY (US); Lindsey Bagley, Berkshire (GB); Graham Godfrey, Worcestershire (GB); Hiep Huatan, Maidstone (GB)

(73) Assignee: Church & Dwight Co., Inc., Princeton, NJ (US)

( * ) Notice: Subject to any disclaimer, the term of this patent is extended or adjusted under 35 U.S.C. 154(b) by 0 days.

(21) Appl. No.: 15/092,332

(22) Filed: Apr. 6, 2016

(65) Prior Publication Data
US 2016/0296470 A1 Oct. 13, 2016

Related U.S. Application Data

(60) Provisional application No. 62/144,224, filed on Apr. 7, 2015, provisional application No. 62/238,947, filed on Oct. 8, 2015.

(51) Int. Cl.
*A61K 9/00* (2006.01)
*A61K 45/06* (2006.01)
(Continued)

(52) U.S. Cl.
CPC .............. *A61K 9/0056* (2013.01); *A23G 3/36* (2013.01); *A23G 3/54* (2013.01); *A61K 9/2009* (2013.01);
(Continued)

(58) Field of Classification Search
CPC .................................................. A61K 9/0056
See application file for complete search history.

(56) References Cited

U.S. PATENT DOCUMENTS

| 5,004,595 A | 4/1991 | Cherukuri et al. |
| 5,690,990 A | 11/1997 | Bonner et al. |
| (Continued) | | |

FOREIGN PATENT DOCUMENTS

| CN | 1325274 A | 12/2001 |
| CN | 1352526 A | 6/2002 |
| (Continued) | | |

OTHER PUBLICATIONS

"Fat and Oil Melt Point Temperatures", downloaded from the web on Jan. 8, 2021. (Year: 2021).*
(Continued)

*Primary Examiner* — Isis A Ghali
(74) *Attorney, Agent, or Firm* — Church & Dwight Co., Inc.

(57) ABSTRACT

The present disclosure provides oral, chewable dosage forms that are suitable for delivery of one or more active ingredients to a consumer, particularly a human individual. The dosage forms can be configured as multicomponent compositions formed of a first component including a gummy composition, at least one further component including a composition that is different from the gummy composition, and an active ingredient. The gummy composition and the second composition can be co-deposited to form multicomponent dosage forms wherein a gummy shell at least partially surrounds a core that is solid or liquid at standard temperature.

17 Claims, 1 Drawing Sheet

(51) Int. Cl.

| | |
|---|---|
| *A61K 33/42* | (2006.01) |
| *A23G 3/36* | (2006.01) |
| *A23G 3/54* | (2006.01) |
| *A61K 9/20* | (2006.01) |
| *A61K 31/167* | (2006.01) |
| *A61K 31/19* | (2006.01) |
| *A61K 31/197* | (2006.01) |
| *A61K 31/375* | (2006.01) |
| *A61K 31/4545* | (2006.01) |
| *A61K 31/519* | (2006.01) |
| *A61K 31/616* | (2006.01) |

(52) U.S. Cl.
CPC .......... *A61K 9/2013* (2013.01); *A61K 9/2018* (2013.01); *A61K 9/2027* (2013.01); *A61K 9/2054* (2013.01); *A61K 9/2072* (2013.01); *A61K 31/167* (2013.01); *A61K 31/19* (2013.01); *A61K 31/197* (2013.01); *A61K 31/375* (2013.01); *A61K 31/4545* (2013.01); *A61K 31/519* (2013.01); *A61K 31/616* (2013.01); *A61K 33/42* (2013.01); *A61K 45/06* (2013.01); *A23V 2002/00* (2013.01)

(56) References Cited

U.S. PATENT DOCUMENTS

| | | | |
|---|---|---|---|
| 5,759,599 | A | 6/1998 | Wampler et al. |
| 6,039,901 | A | 3/2000 | Soper et al. |
| 6,045,835 | A | 4/2000 | Soper et al. |
| 6,056,992 | A | 5/2000 | Lew et al. |
| 6,060,078 | A | 5/2000 | Lee |
| 6,106,875 | A | 8/2000 | Soper et al. |
| 6,117,455 | A | 9/2000 | Takada et al. |
| 6,482,433 | B1 | 11/2002 | Deroos et al. |
| 6,929,814 | B2 | 8/2005 | Bouwmeesters et al. |
| 8,404,275 | B2 | 3/2013 | Habboushe |
| 8,414,917 | B2 | 4/2013 | Asano et al. |
| 8,673,190 | B2 | 3/2014 | Snowden et al. |
| 2003/0086960 | A1 | 5/2003 | Seielstad et al. |
| 2003/0219514 | A1 | 11/2003 | Jones et al. |
| 2005/0260329 | A1 | 11/2005 | Yusuf et al. |
| 2006/0263475 | A1 | 11/2006 | Jani et al. |
| 2007/0141198 | A1 | 6/2007 | Yang |
| 2008/0063748 | A1* | 3/2008 | Massey ............... A23G 3/0068 426/6 |
| 2008/0248079 | A1 | 10/2008 | Dempsey et al. |
| 2008/0248089 | A1 | 10/2008 | Bugge |
| 2010/0003390 | A1 | 1/2010 | Rifkin et al. |
| 2010/0034894 | A1 | 2/2010 | Szymczak et al. |
| 2010/0166810 | A1 | 7/2010 | Habboushe |
| 2010/0166914 | A1* | 7/2010 | Herron ............... A23G 1/48 426/61 |
| 2010/0226904 | A1 | 9/2010 | Davis |
| 2010/0330058 | A1 | 12/2010 | Davis |
| 2012/0035277 | A1 | 2/2012 | Davis |
| 2013/0136792 | A1* | 5/2013 | Draper ............... A61P 3/06 424/452 |
| 2013/0189361 | A1 | 7/2013 | Habboushe |
| 2013/0209540 | A1 | 8/2013 | Duggins et al. |
| 2013/0287899 | A1 | 10/2013 | Rifkin |
| 2013/0316053 | A1 | 11/2013 | Rifkin |
| 2014/0271853 | A1 | 9/2014 | Hall et al. |
| 2016/0045433 | A1 | 2/2016 | Whitney |

FOREIGN PATENT DOCUMENTS

| | | |
|---|---|---|
| CN | 1655770 A | 8/2005 |
| CN | 101686931 A | 3/2010 |
| CN | 102813275 A | 12/2012 |
| EP | 1136067 A1 | 9/2001 |
| WO | 98/20860 A2 | 5/1998 |
| WO | 00/61116 A2 | 10/2000 |
| WO | 2009007769 A1 | 1/2009 |
| WO | 2012106582 | 8/2012 |
| WO | 2012126770 A1 | 9/2012 |
| WO | 2013136183 A2 | 9/2013 |

OTHER PUBLICATIONS

International Search Report and Written Opinion for PCT Application No. PCT/US16/26228, dated Jul. 1, 2016, pp. 1-10, which corresponds to this current application.

International Search Report and Written Opinion for PCT Application No. PCT/US16/26219, dated Jul. 12, 2016, pp. 1-11, which corresponds to this current application.

Iwamoto, et al., "Preparation of Gelatin Microbeads With a Narrow Size Distribution Using Microchannel Emulsification", AAPS PharmSciTech 2002; 3 (3) article 25 (http://www.aapspharmscitech. org)., published Aug. 8, 2002, pages 1-5.

Singh, et al., "Microencapsulation: A promising technique for controlled drug delivery" Res Pharm Sci. Jul.-Dec. 2010; 5(2): published Jun. 1, 2010, pp. 65-77.

Chen, et al., "Food Technology (3rd Edition)", China Light Industry Press, p. 290, Mar. 2014. CN.

Jin, et al., "Food Properties", China Science and Technology Press, pp. 3 and 7, Apr. 1991. CN.

Zhao, "Food Technology (2nd Edition)", China Industry Press, p. 613, Nov. 1999. CN.

English Translation of Decision of Rejection dated May 13, 2021 in corresponding CN Application No. 201680029868.1 wherein NPL References are discussed therein.

* cited by examiner

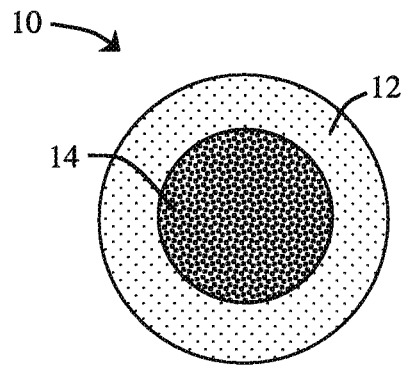
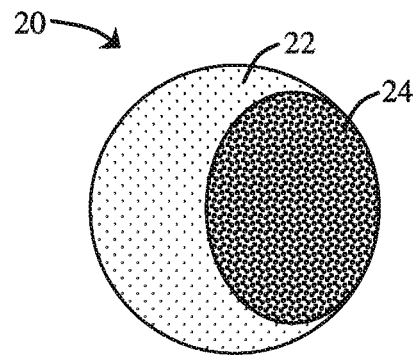
FIG. 1          FIG. 2
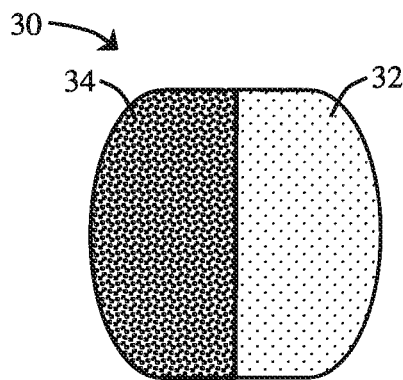
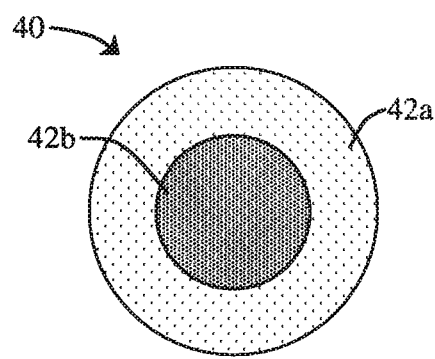
FIG. 3          FIG. 4
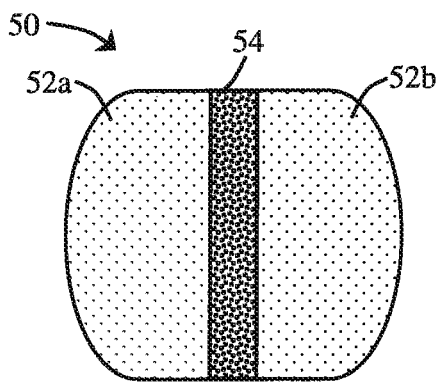
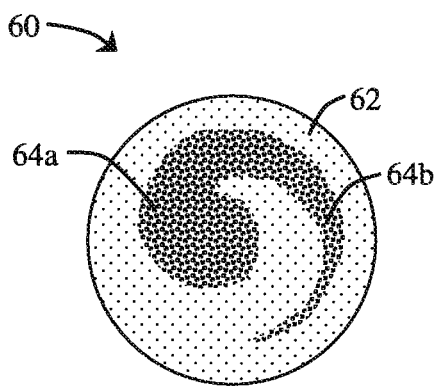
FIG. 5          FIG. 6

MULTICOMPONENT GUMMY COMPOSITIONS WITH SOFT CORE

FIELD OF THE DISCLOSURE

The present disclosure relates to orally ingestible dosage forms. The dosage forms can comprise at least two different compositions include a multicomponent unit in a variety of combinations.

BACKGROUND

Oral dosing of many materials with desirable properties and functions can be problematic when provided in a chewable form because the intrinsic taste of such materials can be unpleasant, particularly to children. The intrinsic bitterness of certain active pharmaceutical ingredients (APIs) in particular can present a major obstacle to the acceptance, compliance, and effectiveness of treatments including oral, chewable dosing.

Previous approaches to addressing the problem of poor palatability of certain materials have been based mainly on nullifying undesirable tastes using flavor additives, chemical chelation (e.g., using ion exchange resins and β-cyclodextrins) and physical encapsulation. These systems can be adapted into solid dosage forms or liquid based formulations as solutions, suspensions, or multi-phase emulsions.

Generally, most children cannot swallow traditional solid dosage forms (e.g., tablets and capsules) at least until the age of six due to the risk of choking. For young children (i.e., <2 years of age), liquid dosage forms are preferred as dosing can be facilitated via an oral syringe or spoon. These dosage forms, however, can be problematic as they accentuate the taste issue of bitter active ingredients in solution. Suspensions can improve taste-masking effectiveness, however, mouth feel and grittiness is often the overriding issue.

Alternative non-liquid formulations have been designed to compensate for the poor dosing acceptability and taste limitation of liquid-based formulations for older children (>2 years of age). These formulations typically can include chewable tablets, gummies, specially compounded lollipops, and other confectionery mimics.

Gummy dosage forms are particularly effective for enabling compliant dosing in children as they provide a palatable, chewable base and can incorporate active ingredient(s) that are generally of very low dose, have the ability to withstand the high thermal stress of the gummy manufacturing process, and have low intrinsic taste response. Moreover, while gummy dosage forms provide the basis for effective dosing of active ingredients to children, their application for the delivery of APIs and like materials has been highly restrictive due to the limited number of active ingredients that are compatible with the gummy dosage platform.

Gummy dosage forms have previously been produced by compounding a variety of ingredients (e.g., sugars, corn syrup, water, gelatin, flavors, and other sweeteners) then cooking the mixture at high temperatures (e.g., up to about 240° C.) before depositing the cooked mixture into pre-formed molds. The incorporation of the active ingredients can be facilitated only during the initial compounding step prior to cooking. The viscosity of the cooked mixture is generally too high to enable the active ingredients to be added retrospectively. As a result of the very high thermal stress of the cooking process, the active ingredients can be subject to significant chemical and/or physical degradation during the manufacture of gummies. Accordingly, the practice of utilizing overages (including excess active ingredient to off-set the losses due to degradation during manufacturing) has been instituted.

The use of overages to off-set gross manufacturing losses in gummy dosage forms is permitted only for some functional actives that do not present safety concerns. The application of this practice for APIs is not generally feasible as it may lead to significant efficacy, safety, and regulatory issues. In addition, as the quality control requirements for APIs (i.e., claimed dose of active, content uniformity, degradation limits, etc.) are generally much more stringent than food-based functional additives, the suitability of gummies as an oral delivery platform becomes even more prohibitive. As such, there remains a need in the art for oral, chewable dosage forms suitable for delivery of APIs and the like in a manner where active ingredient content can be closely controlled throughout manufacturing to provide a resulting dosage form of consistent quality and desirable palatability.

SUMMARY OF THE DISCLOSURE

The present disclosure provides chewable, multicomponent dosage forms that are adapted for the delivery of a wide variety of active ingredients to individuals that may have difficulty in swallowing conventional oral dosage forms (e.g., children and geriatric adults) and/or those who have an aversion to the taste of the active ingredients or have dosing fatigue to swallowable pills. The present disclosure provides for formulations of active ingredients in dosage forms that are stable on storage under ambient conditions and have improved palatability attributes over conventional oral dosage forms such as tablets and capsules.

In one or more embodiments, a multicomponent composition according to the present disclosure can be configured for oral administration, and can particularly provide improved palatability for an active ingredient that can be included in the composition. For example, the multicomponent composition can comprise: a chewable, multicomponent composition for oral administration, the multicomponent composition comprising: a first component that is a gummy composition; a second component that is a composition in a liquid form or a composition that is substantially solid at a temperature of about 35° C. or less and is a viscous fluid at a temperature of about 40° C. to about 100° C.; and an active ingredient; wherein the second component is at least partially surrounded by the first component. In one or more embodiments, such multicomponent composition can be further defined in relation to one or more of the following statements, which statements may be combined in any number and order.

The multicomponent composition can be substantially in a core/shell conformation with the first component forming a shell surrounding at least one core formed of the second component.

The first component can have a thickness, measured as the distance between an outer surface of the second component (e.g., in the form of at least one core), and an outer surface of the first composition, of about 1 mm or greater at all points.

The active ingredient can be included in the second component.

The active ingredient can be included in the first component.

One or more active ingredients (different or the same) can be included in both the first component and the second component.

A plurality of active ingredients can be included in the multicomponent composition.

An active ingredient can be included in the first component and an active ingredient can be included in the second component.

The active ingredient can be a natural or synthetic substance that is recognized as being beneficial to human health.

The active ingredient can be selected from the group consisting of non-steroidal anti-inflammatory drugs (NSAIDs), analgesics, antihistamines, decongestants, antitussives, expectorants, sleep aids, antibiotics, laxatives, antidiarrheals, anthelmintics, antacids, vitamins, minerals, phytonutrients, fiber, fatty acids, amino acids, polypeptides, botanicals, herbs, prebiotics, probiotics, and combinations thereof.

The gummy composition of the first component can be elastic or viscoelastic.

The gummy composition can comprise about 70% to about 94% w/w of one or more hydrophilic bulking agents, about 1% to about 20% w/w of one or more hydrophilic, long-chain polymers, and about 5% to about 35% w/w of a water source.

The one or more hydrophilic bulking agents can comprise one or more saccharides or saccharide derivatives.

The one or more hydrophilic bulking agents can include one or more hydrogenated carbohydrates.

The one or more hydrophilic bulking agents can include one or both of sugar solids and granulated sugar.

The one or more hydrophilic bulking agents can include glucose, sucrose, and sorbitol.

The active ingredient can be in an encapsulated form.

The second component can have a viscosity of about 0.01 to about 30 PaS at a temperature of about 50° C. The viscosity can be as measured using a TA Instruments AR500 rheometer. The viscosity can be as measured across a shear rate of 3.5 $s^{-1}$ to 982 $s^{-1}$.

The second component can comprise a lipidic base in an amount of about 20% to about 70% by weight of the second component and one or more hydrophilic bulking agents in an amount of about 10% to about 70% by weight of the second component.

The hydrophilic bulking agent and the lipidic base can be present in a ratio of about 0.2 to about 0.8.

The lipidic base can be a fat or oil from one or more of a vegetable source, an animal source, a nut source, and a seed source.

The lipidic base can be a fat or oil from one or more of cocoa, palm, and coconut.

The hydrophilic bulking agent can comprise a material selected from the group consisting of saccharides, saccharide derivatives, hydrogenated carbohydrates, emulsifiers, proteins, processing aids, inorganic salts, active ingredients, and combinations thereof.

The hydrophilic bulking agent can be selected from the group consisting of sucrose, glucose, dextrose, maltose, variations thereof, and combinations thereof.

The hydrophilic bulking agent can be selected from the group consisting of sorbitol, glycerol, mannitol, maltitol, erythritol, lactitol, isomalt, and combinations thereof.

The second component can comprise a hydrophilic bulking agent in an amount of about 30% to about 90% by weight of the second component.

The second component can be substantially hydrophilic and thus can include substantially no lipidic base.

The hydrophilic bulking agent in a substantially hydrophilic second component can be selected from the group consisting of saccharides, saccharide derivatives, hydrogenated carbohydrates, and combinations thereof.

The first component can have a water activity $a_w 1$, the second component can have a water activity $a_w 2$, and the value of $a_w 1$ can be greater than $a_w 2$ prior to combining the first component and the second component.

The value of $a_w 1$ can be greater than the value of $a_w 2$ by at least 0.05.

The value of $a_w 1$ can be about 0.65 or Greater.

The value of $a_w 1$ can be about 0.5 to about 0.65.

The gummy composition can have a solids content of at least about 78% by weight

The second component expressly may not be in the form of a compressed mass of solid particles.

In one or more embodiments, the present disclosure may relate to methods for forming a multicomponent composition. For example, the method can comprise: providing a liquid gummy composition at a temperature that is greater than a gelling temperature of the gummy composition; providing a core composition in the form of a viscous fluid at a temperature that is less than the gelling temperature of the gummy composition; and co-depositing the core composition with the gummy composition so that the core composition is substantially surrounded by the gummy composition. In one or more embodiments, such method can be further defined in relation to one or more of the following statements, which statements may be combined in any number and order.

The co-depositing can be carried out such that the gummy composition is cooled to below its gelling temperature within a time of about 30 seconds or less.

The gummy composition can be maintained at a temperature of about 95° C. or greater prior to the co-depositing.

Prior to the co-depositing, the core composition can be maintained at a temperature that is greater than a melting temperature of the core composition and is less than about 60° C.

The gummy composition can have a density prior to the co-depositing, and the core composition can have a density prior to the co-depositing, and the respective densities can differ by no more than about 25%.

The co-depositing can be carried out at a temperature of about 35° C. to about 60° C.

The core composition can have a viscosity of about 0.01 to about 30 PaS at a temperature of about 50° C.

In one or more further embodiments, the present disclosure can provide chewable dosage forms that have improved stability. Such stability can arise from careful choice of compositions with defined water activities. In some embodiments, an oral, chewable dosage form can comprise an outer gummy composition substantially surrounding a core composition, the outer gummy composition having a water activity $a_w 1$, and the core composition having a water activity $a_w 2$; wherein the value of $a_w 1$ is greater than $a_w 2$ prior to combining the core composition with the outer gummy composition. In one or more embodiments, such dosage form can be further defined in relation to one or more of the following statements, which statements may be combined in any number and order.

The core composition can be a liquid composition or a solid composition at a temperature of about 35° C. or less and be a viscous fluid at a temperature of about 40° C. to about 100° C.

The value of $a_w 1$ can be greater than $a_w 2$ by at least 0.05.

The value of $a_w 1$ can be about 0.5 to about 0.65.

The gummy composition can comprise about 70% to about 94% w/w of one or more hydrophilic bulking agents, about 1% to about 20% w/w of one or more hydrophilic, long-chain polymers, about 5% to about 30% w/w of a hydrogenated carbohydrate, and about 5% to about 35% w/w of a water source.

The gummy composition can have a solids content of at least about 78% by weight.

The oral, chewable dosage form further can comprise an active ingredient that is a natural or synthetic substance that is recognized as being beneficial to human health.

The active ingredient can be selected from the group consisting of non-steroidal anti-inflammatory drugs (NSAIDs), analgesics, antihistamines, decongestants, antitussives, expectorants, sleep aids, antibiotics, laxatives, anti-diarrheals, anthelmintics, antacids, vitamins, minerals, phytonutrients, fiber, fatty acids, amino acids, polypeptides, botanicals, herbs, prebiotics, probiotics, and combinations thereof.

The second component can comprise a lipidic base in an amount of about 20% to about 70% by weight of the second component and one or more hydrophilic bulking agents in an amount of about 10% to about 70% by weight of the second component.

The hydrophilic bulking agent and the lipidic base can be present in a ratio of about 0.2 to about 0.8.

The lipidic base can be a fat or oil from one or more of a vegetable source, an animal source, a nut source, and a seed source.

The hydrophilic bulking agent can comprise a material selected from the group consisting of saccharides, saccharide derivatives, hydrogenated carbohydrates, emulsifiers, proteins, processing aids, inorganic salts, active ingredients, and combinations thereof.

The second component can comprise a hydrophilic bulking agent in an amount of about 30% to about 90% by weight of the second component.

The hydrophilic bulking agent can be selected from the group consisting of saccharides, saccharide derivatives, hydrogenated carbohydrates, and combinations thereof.

BRIEF DESCRIPTION OF THE FIGURES

FIG. 1 is a cross-section of a multicomponent composition according to an exemplary embodiment of the present disclosure illustrating a gummy composition completely surrounding a second composition in a shell/core configuration;

FIG. 2 is a cross-section of a multicomponent composition according to an exemplary embodiment of the present disclosure illustrating a gummy composition partially surrounding a second composition;

FIG. 3 is a cross-section of a multicomponent composition according to an exemplary embodiment of the present disclosure illustrating a gummy composition and a second composition substantially in a side-by-side configuration;

FIG. 4 is a cross-section of a multicomponent composition according to an exemplary embodiment of the present disclosure illustrating a first gummy composition surrounding a second gummy composition;

FIG. 5 is a cross-section of a multicomponent composition according to an exemplary embodiment of the present disclosure illustrating a second composition between two gummy compositions FIG. 6 is a cross-section of a multicomponent composition according to an exemplary embodiment of the present disclosure illustrating a gummy composition and a second composition that is partially blended into the gummy composition.

DETAILED DESCRIPTION OF THE DISCLOSURE

The invention now will be described more fully hereinafter through reference to various embodiments. These embodiments are provided so that this disclosure will be thorough and complete, and will fully convey the scope of the invention to those skilled in the art. Indeed, the invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present disclosure relates to oral, multicomponent dosage forms that are suitable for delivery of active ingredients in a manner that is highly palatable and that thusly improves compliance with dosing requirements for the active ingredients. In one or more embodiments, the dosage forms can comprise a gummy composition as at least one of the components. The gummy composition may completely or at least partially surround one or more different compositions that are also included in the multicomponent dosage form. While two or more different gummy compositions may be used, in some embodiments, multicomponent dosage forms of the present disclosure can comprise at least one gummy composition and at least one different composition that is also in a different form. Such different composition can be referred to as a second composition (the gummy composition being a first composition). The multicomponent compositions thus may comprise at least two, at least three, at least four, or even more different compositions. The active ingredient can be included in the gummy composition, in the one or more different composition, or in the gummy composition and one or more of the different composition(s).

A "gummy" as used herein is understood to refer to a confectionery that can be defined by its compositional nature, as otherwise described herein, and also by its chewy texture and mouthfeel. Gummy bears, gummy worms, and other gummy candies are known in the art, and a person of ordinary skill in the art would understand the term "gummy" to refer to a composition having such texture and mouthfeel.

An "active ingredient" as used herein can include any compound, composition, or like material that may be included in a dosage form for delivery to an individual to achieve any one or more of a desired nutritional purpose, medicinal purpose, and therapeutic purpose. In some embodiments, an active ingredient can be an APL Non-limiting examples of APIs include non-steroidal anti-inflammatory drugs (NSAIDs—e.g., ibuprofen, diclofenac, and naproxen), analgesics (e.g., acetaminophen, aspirin), antihistamines, decongestants, antitussives, expectorants, sleep aids, antibiotics, laxatives, anti-diarrheals, anthelmintics, and antacids. Further, non-limiting examples of materials that may be included as an active ingredient include vitamins, minerals, phytonutrients (e.g., carotenoids, flavonoids, resveratrol, and glucosinolates), fiber, fatty acids, amino acids, polypeptides, and botanicals. An active ingredient can include any plant-derived material that is safe for human consumption, including herbal extracts, botanical extracts, and the like. Other materials, such as prebiotics and probiotics, can also be used as an active ingredient. In some embodiments, an active agent according to the present disclosure may be classified as dietary supplement according to the Dietary Supplement Health and Education Act of 1994, whereby a dietary supplement is defined to mean a product (other than tobacco) intended to supplement the diet that bears or contains one or more of the following dietary ingredients: a vitamin, a mineral, an herb or other botanical, an amino acid, a dietary substance for use by man to supplement the diet by increasing the total dietary intake, or a concentrate, metabolite, constituent, extract, or combination of any of the aforementioned ingredients.

The multicomponent dosage forms can be configured with the different compositions combined in a variety of conformations. In some embodiments, the gummy composition may partially or completely surround the second composition. For example, FIG. 1 illustrates a multicomponent composition 10 wherein a gummy composition 12 completely surrounds a second composition 14, thus forming a shell/core configuration. FIG. 2 illustrates, as a further example, a multicomponent composition 20 wherein a gummy composition 22 partially surrounds a second composition 24, and FIG. 3, for example, illustrates a multicomponent composition 30 wherein a gummy composition 32 and a second composition 34 are substantially in a side-by-side configuration. In a further example shown in FIG. 4, a first gummy composition 42a can surround a second gummy composition 42b. In such embodiments, one or more active agents may be included in one or both of the compositions. As before, the first gummy composition can completely or partially surround the second gummy composition, or the gummy compositions may be in a side-by-side arrangement. In some embodiments, the multicomponent dosage form can comprise a plurality of layers. In some embodiments, a stacked configuration may be utilized. For example, as seen in FIG. 5, the multicomponent composition 50 can comprise a second composition 54 between two gummy compositions 52a and 52b. It is understood that the reverse situation is also encompassed wherein a gummy composition may be provided between two different compositions (i.e., between two layers of the second composition or between a layer of the second composition and a layer of a third composition).

In one or more embodiments, a dosage form as described herein can be adapted to compartmentalize the active ingredient into a portion of the overall dosage form that is separate from the gummy composition. A compartmentalized gummy dosage form can afford stability for the active ingredient(s) and can permit consistent release of the actives from the gummy dosage form while also providing optimal organoleptic response to aid user acceptance and compliance. Compartmentalization is further beneficial for any one or more of the following: the active ingredients are not subject to the same thermal stress that is imparted on the gummy base during the cooking and depositing process; the active ingredients are physically separated from the gummy base to limit the potential for chemical and physical interactions during the manufacture and following long-term storage; the active ingredients can be controlled to a high quality limit in respect of dose, dose uniformity, and degradation limit compared to the gummy base; and the active ingredients are subject to no overage inclusion or only limited overage inclusion to take account of gross losses during manufacture. While it is thus evident that compartmentalization can be beneficial, in one or more embodiments, active ingredients can be included in a gummy composition, particularly if the above considerations are not critical to the overall nature of the dosage form. Likewise, active ingredients may be present in the gummy composition and/or in any one or all of one or more further compositions included in the multicomponent dosage form.

Where compartmentalization is desirable, the multicomponent dosage forms of the present disclosure can be particularly useful. For example, a compartmentalized gummy dosage form can be configured such that the active ingredient is partially or completely present within a second composition that is provided in combination with the gummy composition. Separating the active ingredient from the gummy base via compartmentalization in the second composition allows the active ingredient (within the second composition) to be incorporated into the gummy dosage form while substantially avoiding the high thermal stress inherent to the cooking step in preparing the gummy composition. In addition, by separating the compounding step for the second composition from the manufacturing process for the gummy composition (particularly one or more deposition steps), the control of the key quality attributes for the active ingredient is not limited by the inflexible and stress-bound process for forming the gummy composition.

Although compartmentalization can be advantageous, it is not required. In some embodiments, the different compositions forming the multicomponent dosage forms can be partially blended or otherwise combined so that the second composition is not necessarily in the form of a discrete "unit" within the gummy composition. As a non-limiting example, as seen in FIG. 6, the multicomponent composition 60 can comprise a gummy composition 62 and a second composition 64 that is partially blended into the gummy composition. As illustrated, the second composition 64 has a main body 64a and a tail 64b that substantially blends into the gummy composition. Such conformation may be referred to as a "swirl," and other like structures are also encompassed by the present disclosure.

The nature of the second composition can be particularly relevant in providing the significant advantages over conventional gummy matrix formulations. In particular, the second composition can be provided with specific properties that confer consistent release of the active ingredient and maximize the organoleptic response of the overall gummy dosage form.

In the multicomponent dosage forms of the present disclosure, the gummy composition, in some embodiments, can be configured according to known recipes. For example, it is generally known to prepare a gummy composition by combining gellants, sweeteners, water, colors, and flavors. The combined materials can be heated to form a thickened slurry, which can then be poured into molds to provide the desired shape. The molds may be coated with a release agent. The formed gummy compositions are allowed to cool and set to the final, desired shape when released from the molds. If desired, one or more coating layers can be applied to the formed gummy composition.

In one or more embodiments, a gummy composition utilized according to the present disclosure can be a hydrocolloid system. In particular, a hydrocolloid system can comprise one or more hydrophilic long-chain polymers, one or more hydrophilic bulking agents, and a water source. Optionally, the hydrocolloid system can include one or more further ingredients, such as pH modifiers, coloring agents, and/or flavoring agents. The outer composition particularly can be substantially a gummy base. The outer composition may particularly be characterized as being an elastic or viscoelastic material.

Hydrophilic, long-chain polymers useful in a hydrocolloid system according to the present disclosure include long chain carbohydrates (e.g., polysaccharides) as well as various proteins. The hydrophilic, long-chain polymer preferably is configured to thicken and form a gel upon hydration (with or without heating). Non-limiting examples of hydrophilic, long-chain polymers that may be included in a hydrocolloid system for use as a gummy composition according to the present disclosure include: gelatin, pectin, carrageenan, gellan gum, locust bean gum, gum arabic, xanthan gum, starch, methylcellulose, agar, konjac, alginates, and combinations thereof (including single, binary, tertiary, or quaternary blends).

Hydrophilic bulking agent useful in a hydrocolloid system according to the present disclosure include saccharides or saccharide derivatives as otherwise described herein. In exemplary embodiments, hydrophilic bulking agents can include oligofructose, dextrins, monosaccharides (e.g., fructose or glucose), disaccharides (e.g., palatinose or sucrose), hydrogenated carbohydrates, also known as sugar alcohols (e.g., polyols, monosaccharide alcohols, disaccharide alcohols, or oligosaccharide alcohols), and syrups (e.g., glucose syrup or fructose syrup). The hydrophilic bulking agent further may be a synthetic material, such as soluble fibers (e.g., polydextrose).

The hydrating materials used in the hydrocolloid system can include any variety of materials configured to donate water to the hydrophilic, long-chain polymer. The hydrating material particularly can be substantially pure water, however, the hydrating material may be an aqueous composition including one or more additives, such as a syrup, a fruit juice, or a flavoring liquid.

In some embodiments, a pH modifier particularly can be an acidifier. Non-limiting examples of acidic materials that may be used include citric acid, malic acid, lactic acid, tartaric acid, fumaric acid, phosphoric acid, ascorbic acid, sodium bisulfate, and combinations thereof.

The relative amount of the components utilized in a gummy composition can vary. The following embodiments exemplify the relative amounts of the components that may be utilized. All percentages are on a weight/weight basis (the weight of the specific component relative to the total weight of the gummy composition).

The gummy composition can comprise about 70% to about 94%, about 75% to about 90%, or about 78% to about 86% w/w of the hydrophilic bulking agent(s), particularly one or more saccharides or saccharide derivatives. Within the above ranges, the hydrophilic bulking agent(s) can comprise: about 1% to about 30%, about 5% to about 20%, or about 8% to about 18% w/w of one of more hydrogenated carbohydrates; about 10% to about 70%, about 15% to about 65%, or about 20% to about 60% w/w of sugar syrup solids; about 10% to about 70%, about 15% to about 65%, or about 20% to about 60% w/w of granular sugar.

The gummy composition can comprise about 1% to about 20%, about 1% to about 15%, or about 2% to about 7% w/w of the one or more hydrophilic, long-chain polymers.

The gummy composition can comprise about 5% to about 35%, about 10% to about 25%, or about 16% to about 22% w/w of water.

The gummy composition can comprise up to about 2%, up to about 1.5%, or up to about 1% w/w of a pH modifier. More particularly, about 0.1% to about 1%, about 0.2% to about 0.8%, or about 0.3% to about 0.6% w/w of the pH modifier can be used.

The gummy composition can comprise up to about 4%, up to about 2%, or up to about 1% of coloring agents.

The gummy composition can comprise up to about 4%, up to about 2%, or up to about 1% of flavoring agents.

In a non-limiting example, a gummy composition can comprise about 1% to about 4% by weight of pectin; 0% to about 3% by weight of further hydrophilic, long-chain polymers (e.g., starch, gelatin, carrageenan, cellulosic material, agar, or gelan); about 10% to about 70% by weight sugar syrup solids (e.g., glucose syrup solids); about 10% to about 70% by weight granular sugar (e.g., sucrose); about 0% to about 30% by weight of hydrogenated carbohydrates (e.g., sorbitol syrup, glycerol, mannitol, maltitol, erythritol, isomalt); about 0.1% to about 1.5% by weight citric acid (or other pH modifier); and the balance water, with weights being based on the total weight of the gummy composition.

The nature of the gummy composition used in forming the multicomponent dosage forms discussed herein can cause the dosage forms to be substantially chewable. A "chewable" dosage form, while capable of being swallowed whole, is configured specifically for chewing prior to swallowing. As such, a chewable dosage form is specifically distinguishable from a non-chewable dosage form, such as a vitamin tablet or capsule that is intended to be swallowed whole. In some embodiments, the term chewable can thus mean that the dosage form is intended to be retained in the mouth of the consumer for a period of time prior to swallowing during which time the dosage form may undergo a change in structure that facilitates ease of swallowing. The chewable dosage form may thus be reduced to smaller pieces through mastication. In some embodiments, the chewable dosage form may be configured to at least partially dissolve within the mouth of the consumer. As such, the chewable dosage form may also be dissolvable and may thus be referred to as a "melt-away" form.

The second composition used in the multicomponent dosage forms of the present disclosure can be provided in a variety of forms and combinations of materials. As such, the multicomponent dosage form can be configured as needed to achieve not only the desired delivery of one or more active ingredients but also to provide one or more desired organoleptic properties. For example, the second composition may be in a form such that it has a texture that is substantially different from the texture of the gummy composition or a form such that it has a texture that is substantially the same as the texture of the gummy composition. In one or more embodiments, the second composition (or one or more further compositions) may be provided in a form such that, at standard temperature, the second composition is a substantially soft (i.e., non-brittle) solid or semi-solid material, is substantially resilient, is substantially chewy, or is substantially liquid, semi-solid or otherwise in the form of a viscous fluid above 40° C. Similarly, the second composition (or one or more further compositions) can have a taste that is complimentary or contrasting to the gummy composition. For example, where the gummy composition is typically sweet, the second composition may be substantially sour. A variety of flavor and taste combinations can be prepared in light of the present disclosure.

It is understood that the multicomponent dosage forms of the present disclosure may be configured for undergoing changes under mouth conditions. Discussion herein of "mouth conditions" can relate to one or more characteristics (in any combination) associated with the presence of an item in the mouth of an individual. For example, mouth conditions can include any combination of temperature, moisture, and pH typically found in the mouth of a human as well as the shear, compression, and other mechanical forces that may be applied by the teeth during chewing. Mouth conditions particularly can relate to being in contact with saliva.

In some embodiment, mouth conditions can particularly mean contact with saliva at the temperature and pH typically present in the human mouth.

The nature of the second composition can be at least partially related to the processability of the composition. For example, as further discussed herein, the multicomponent dosage forms of the present disclosure can be prepared via co-deposition of a gummy composition and a second composition. As such, the second composition preferably is adapted to be a liquid or a viscous fluid within a processing temperature range. For example, the second composition can be adapted to be a liquid composition at normal storage temperatures (e.g., at temperatures below about 35° C. and preferably greater than 0° C.) and remain a liquid composition at higher processing temperatures (e.g., in the range of about 40° C. to about 100° C.). Further, the second composition can be adapted to be substantially solid (e.g., a solid or a semi-solid composition) at a temperature of about 35° C. or less and be a viscous fluid at a temperature of about 40° C. or greater. For example, the second composition can be adapted to be a liquid as noted above or be a viscous fluid as noted above at a temperature within the range of about 40° C. to about 100° C., about 42° C. to about 80° C., or about 45° C. to about 70° C. In embodiments wherein a substantially solid second composition is adapted to transition to a viscous fluid, such second composition need not necessarily be a viscous fluid at all points within the defined temperature range. For example, a composition that is a solid or semi-solid material below a temperature of 50° C. but that transitions to a viscous fluid above 50° C. (but still within the above-noted temperature range) would be considered to be a viscous fluid within the above-noted ranges. Thus, the second composition may be adapted to be a liquid under processing conditions and under storage conditions (e.g., a temperature of about 35° C. or less), or the second composition may be adapted to be a liquid under processing conditions but be a solid or semi-solid under storage conditions. The term "semi-solid" can be synonymous with the term quasi-solid, both of which are intended to refer to materials that exhibit qualities of typical solids (e.g., adapted to support its own weight and hold a defined shape) as well as exhibit some qualities of a liquid (e.g., adapted to conform its shape and/or become at least partially flowable under application of pressure). A semi-solid may be defined in some embodiments as an amorphous solid. As such, the compositions used as the second component can, in various embodiments, be amorphous solids or crystalline solids or be partially amorphous and partially crystalline. In some embodiments, the temperature at which a substantially solid composition suitable for use herein transitions to being a viscous liquid can be considered the melting point of the substantially solid material.

A second composition can be substantially lipophilic as defined by including a major component that is a lipidic base. Non-limiting examples of lipidic bases include oils, fats, and compositions formed therewith. Lipophilic compositions can exist in a molten phase, a solid phase, or a semi-solid phase, and the transition between the phases can be achieved at temperatures wherein the lipid-based composition can provide specific textural properties. For example, it can be desirable for the lipophilic composition to be a soft solid at typical room temperatures but be molten at higher temperatures to facilitate manufacturing. The lipophilic compositions can be configured so that, in a molten form, other components, including powdered or other particulate materials, can be easily combined therewith, such as to form a dispersion. The lipid based compositions can be configured to be a substantially homogeneous mixture of the lipid and the further ingredients. For example, solids may be homogeneously dispersed in the lipid base.

Suitable lipidic materials for use in forming lipophilic compositions include fats and oils derived from one or more of a vegetable source, an animal source, a nut source, a seed source, and the like. Suitable lipidic material may be predominately or completely saturated, predominately or completely unsaturated, or hydrogenated. Non-limiting examples of suitable lipidic materials include fats and/or oils derived from one or more of the following: cocoa, palm, coconuts, almonds, cashews, hazelnuts, macadamia nuts, peanuts, pecans, pistachios, walnuts, pumpkin seeds, sesame seeds, soybeans, rapeseed, corn, safflower seeds, and the like. Embodiments of the second composition that are lipophilic can comprise a lipidic base in an amount of about 20% to about 80%, about 25% to about 75%, or about 30% to about 70% w/w, based on the total weight of the second composition. Specific, non-limiting examples of lipid based materials that may be used in preparing a composition as described herein include chocolates with any cocoa concentration (e.g., milk chocolate, dark chocolate, white chocolate), palm fat, coconut fat, peanut butter, hazelnut fats, vegetable oils, milk fats, confectionery fats (such as available from AAK, AB), and the like. Such materials may include additional components, such as sugar, salt, other oils, and the like. For example, chocolates may comprise sugar, cocoa butter, cocoa processed with alkali, milk fat, lactose (e.g., from milk), soy lecithin, emulsifier, vanillin, artificial flavor, milk, and/or other ingredients. Dairy components utilized in lipophilic compositions can include fats, proteins, and/or sugars derived from cow milk, goat milk, and the like. Suitable lipidic base materials can, in some embodiment, be defined in relation to melting temperature. For example, the lipidic base can have a melting temperature of about 60° C. or less, about 55° C. or less, or about 50° C. or less, such as about 0° C. to about 60° C., about 20° C. to about 60° C., about 5° C. to about 55° C., or about 10° C. to about 50° C.

In one or more embodiments, a second composition that is lipophilic can comprise one or more hydrophilic bulking agents. The hydrophilic bulking agents can be useful to improve one or more rheological properties of the lipidic material, and the hydrophilic bulking agent preferably improves flowability of the lipidic material under processing conditions. For example, a composition formed of substantially 100% by weight lipidic base can be particularly difficult to process for co-deposition with a gummy formulation as described herein; however, the addition of one or more hydrophilic bulking agents can alter the rheology of the lipidic base so as to improve processability thereof. A hydrophilic bulking agent in particular can be useful to alter the dynamic viscosity of a lipid base so as to be within a range as otherwise described herein.

In some embodiments, a second composition that is lipophilic can comprise about 10% to about 70% by weight, about 15% to about 65% by weight, or about 20% to about 60% by weight of one or more hydrophilic bulking agents, said amounts being based on the total weight of the second composition. Preferably, the hydrophilic bulking agent and the lipidic base are present in a ratio of about 0.1 to about 1.1, about 0.15 to about 0.95, about 0.2 to about 0.8, or about 0.25 to about 0.75.

Hydrophilic bulking agents may include saccharides or saccharide derivatives, hydrogenated carbohydrates (e.g., polyols), emulsifiers, proteins, inorganic salts (e.g., di- or tri-calcium phosphates), processing aids, active ingredients, and like materials. A single hydrophilic bulking agent may be used, or a plurality of hydrophilic bulking agents may be used. Specific, non-limiting examples of hydrophilic bulking agents that may be used include sugars, tricalcium phosphate, dicalcium phosphate, active ingredients (e.g., vitamins, minerals, proteins, and bulking diluents), and hydrogenated carbohydrates (e.g., polyols).

In one or more embodiments, the hydrophilic bulking agent can specifically include one or more saccharides or saccharide derivatives. Specific, non-limiting examples include sucrose, glucose, dextrose, maltose, variations thereof, and combinations thereof. The term "variations" is understood to indicate the known, different forms in which such materials may be provided. For example, sugars (e.g., sucrose) may be provided at various levels of processing— e.g., from being granulated to being finely ground (i.e., so-called powdered sugars, icing sugars, and confectionery sugars). Variations may include added components, such as starch or like materials to prevent clumping.

In one or more embodiments, the hydrophilic bulking agent can specifically include one or more hydrogenated carbohydrates. Non-limiting examples include sorbitol, glycerol, mannitol, maltitol, erythritol, lactitol, isomalt.

The term "saccharide" as used herein (including in relation to all compositions described herein) can encompass sugars, starch, and cellulose materials. A saccharide can be a monosaccharide, a disaccharide, an oligosaccharide, or a polysaccharide. Exemplary monosaccharides include glucose, fructose, and galactose. Exemplary disaccharides include sucrose, lactose, lactulose, maltose, trehalose, cellobiose, and chitobiose. Exemplary oligosaccharides include fructo-oligosaccharides, galactooligosaccharides, and mannan oligosaccharides. Exemplary polysaccharides include glucans, starches, celluloses, pectins, xylans, arabinoxylans, mannans, gums (e.g., xanthan), and galactomannans. Saccharide derivatives can include any material that is derived from a saccharide. In particular, saccharide derivatives may be formed by substitution of one or more hydroxyl groups on the compound to form, for example, amino sugars, acidic sugars, deoxy sugars, hydrogenated carbohydrates (also known as sugar alcohols), glycosylamines, and sugar phosphates. Non-limiting examples of hydrogenated carbohydrates include erythritol, xylitol, ribitol, mannitol, sorbitol, volemitol, isomalt, maltitol, and lactitol. Saccharide derivatives can also encompass artificial sweeteners, such as sucralose.

Emulsifiers can include any material suitable to stabilize a mixture of the lipidic base with one or more materials, particularly materials that typically would not form a stable mixture with the lipidic base. Non-limiting examples of emulsifiers include lecithin, monoglycerides, and the like. Further suitable emulsifiers that are generally recognized as safe for products consumed by humans can be found in 21 CFR 178.3400.

A protein as used herein can mean any material formed of a chain of amino acid residues. Non-limiting examples of proteins that may be used as a lipid structuring agent include gelatin, whey, soy, and like materials.

Processing aids as used herein can mean any material recognized in the art as a enhancing the processability of a formulation such as flow enhancers, binders, viscosity modifiers. Non-limiting examples of processing aids that may be utilized include: colloidal silica, polyvinylpyrrolidone (povidone) and polyvinyl alcohol.

A second composition that is lipophilic may include one or more active ingredients as defined herein. For example, the concentration of active ingredients in the lipophilic composition can be about 0.1% to about 60%, about 1% to about 55%, or about 2% to about 50% by weight, based on the total weight of the second composition.

A second composition that is lipophilic may include a defined content of solids. Active ingredients may be solids present in the composition. Cocoa solids, sugar solids, milk solids, nut solids, seed solids, and the like are further examples of solids that may be present. In one or more embodiments, the solids content can be about 1% to about 70%, about 2% to about 60%, or about 5% to about 50% by weight based on the total weight of the second composition. The lipid structuring agent may account for some or all of the solids content.

A second composition that is lipophilic may include preservatives and/or antioxidants to improve the stability of the lipidic base and/or the active ingredients contained therein. Preservatives and antioxidants may comprise: butylated hydroxyanisole (BHA), butylated hydroxytoluene (BHT), ascorbic acid, propyl gallate, tocopherols. When present, preservatives and antioxidants content can be about 0.01% to about 1% w/w of the second composition.

A lipidic composition can take on a variety of forms. For example, the composition may be a dispersion, a suspension, an emulsion, a solution, a mixture, or the like.

Lipophilic compositions as described herein can be particularly useful as carriers for active agents that may be prone to degradation if provided in other types of compositions. For example, beneficial bacteria that are water sensitive may be substantially enclosed in a lipid based composition so as to remain active until consumer ingestion. Likewise, heat and/or light sensitive active agents may benefit from being present in the lipid based composition, which can be provided in a substantially opaque color and which can be formed under conditions with significantly cooler temperatures compared to the manufacture of a gummy composition. Water reactive chemicals (e.g., bicarbonate) also can benefit by being provided within the hydrophobic, lipid based composition. Further, active agents that may degrade or exhibit loss of activity due to contact with water can be included in a lipophilic composition and thus be substantially protected from water present in the gummy composition.

A second component can be hydrophilic as can be defined by the inclusion of a substantial content of water. A hydrophilic composition also may be defined in relation to including substantially no lipidic base (e.g., less than 1%, less than 0.5%, or less than 0.2% w/w based on the total weight of the second component). In some embodiments, water content in a second composition that is hydrophilic can be about 25% or less or about 20% or less by weight based on the total weight of the second composition. More particularly, water content can be about 2% to about 30%, about 5% to about 25%, or about 10% to about 20% by weight based on the total weight of the second composition. In some embodiments, such as where high osmolarity syrups are utilized, water content may be as high as 50%, 60%, or 70% by weight based on the total weight of the second component.

A second composition that is hydrophilic further can comprise a hydrophilic bulking agent. Such hydrophilic bulking agent can be any material that is generally water soluble or water miscible. The hydrophilic bulking agent can be a water structuring agent which, as used herein, can mean a material that mixes with water to form a composition with a viscosity that is greater than the viscosity of pure water, such as at least 5%, at least 10%, at least 20%, or at least 50% greater than the viscosity of pure water. The hydrophilic bulking agent can be present in the second composition in an amount of about 20% to about 95%, about 30% to about 90%, or about 40% to about 80% by weight based on the total weight of the second composition.

A hydrophilic bulking agent can be any such material as otherwise defined in the present disclosure. Non-limiting examples of materials suitable for use as a hydrophilic bulking agent in a second component that is substantially hydrophilic can include saccharides, saccharide- and polysaccharide derivatives, hydrogenated carbohydrates, and like materials. Specific, non-limiting examples of hydrophilic bulking agents include glycerol, sorbitol, sucrose (e.g., granulated sugar, confectionery sugar, and sugar syrups), glucose (including glucose syrups), and hydrogenated starch hydrosylates.

A second composition that is hydrophilic may be defined in some embodiments by its solids content. For example, sugars (e.g., sucrose and glucose), certain lipidic materials (e.g., waxes or paraffins), milk solids, cocoa powders, nut solids, seed solids, and the like are examples of solids that may be present in a hydrophilic composition. In some embodiments, a composition may be considered a high solids composition by having a solids content of about 30% or greater, about 40% or greater, or about 50% or greater by weight, such as about 30% to about 80%, about 35% to about 75%, or about 40% to about 70% by weight based on the total weight of the second composition. Various candies and/or pastilles are examples of materials that may be considered to be high solids compositions. As a non-limiting example, a composition with a high solids content may include 30% to 65% by weight of glucose, 30% to 65% by weight sucrose, 10% to 20% by weight of a lipidic material, 5% to 10% by weight milk solids, and 0% to 5% by weight of hydrocolloids. As another non-limiting example, a composition with a high solids content may include 80% to 90% by weight of a sugar material (e.g., sucrose, glucose syrups, honey, maple syrup) and about 10% to about 20% by weight water.

A second composition that is hydrophilic may include preservatives and/or antioxidants to improve the stability of the composition and/or the active ingredients contained therein. Preservatives and antioxidants may comprise: butylated hydroxyanisole (BHA), butylated hydroxytoluene (BHT), ascorbic acid, propyl gallate, tocopherols. When present, preservatives and antioxidants content can be about 0.01% to about 1% w/w of the second composition.

The second composition, whether lipophilic or hydrophilic, may further include one or more agents adapted to modify, particularly improve, the organoleptic properties of the second composition. For example taste-making agents may be utilized. Non-limiting examples of taste-masking agents include cyclodextrins and ion exchange resins. Further, flavoring agents (natural or artificial) may be utilized. Non-limiting examples of flavoring agents include citric acid; tartaric acid; artificial sweeteners (e.g., acesulfame potassium, aspartame, neotame, saccharine, and sucralose); salts (e.g., sodium chloride); plant extracts (e.g., vanilla, luo han guo); vegetable juice, pulp, and/or extracts; fruit juice, pulp, zest, and/or extracts (e.g., apple, cherry, peach, lemon, lime, orange, grape); berry juice, pulp, and/or extracts (e.g., strawberry, raspberry, blackberry, blueberry); nuts; seeds; warm sensation materials; cool sensation materials; tingling sensation materials; and essential oils. Natural or artificial colors may also be included. Further, one or more antioxidants, preservatives, and/or stabilizers may be included.

In some embodiments, the gummy composition and the second composition can have respective water activities that are sufficiently different so as to reduce or eliminate water transfer between the compositions. Water activity may be defined as the ratio between the vapor pressure of the material or object when placed in a completely undisturbed balance with the surrounding air media and the vapor pressure of distilled water under identical conditions. In one or more embodiments, the gummy composition may be defined by a first water activity $a_w1$, and the second composition may be defined by a second water activity $a_w2$. The respective water activities may be different on initial compounding or at any time prior to combining of the first component and the second component, and the value of $a_w1$ particularly can be greater than the value of $a_w2$. The difference between the value of $a_w1$ and $a_w2$ can be at least 0.025, at least 0.05, at least 0.075, at least 0.1, at least 0.15, or at least 0.2 on initial compounding.

The difference between the respective water activities of the two components may decrease after combination of the components, particularly during storage as $a_w1$ and $a_w2$ reach a substantially common equilibration point. Thus, in some embodiments, it can be beneficial to utilize a gummy composition with a substantially high water content, e.g., $a_w1$ of about 0.65 or greater, about 0.7 or greater, or about 0.75 or greater, such as about 0.65 to 0.99, about 0.7 to about 0.98, or about 0.75 to about 0.95. The water activity of the second composition ($a_w2$) can be about 0.6 or less, about 0.55 or less, or about 0.5 or less, such as about 0.01 to about 0.6, about 0.05 to about 0.55, or about 0.1 to about 0.5.

In one or more embodiments, the rate and extent of transfer of water between the gummy composition and the second composition can be minimized by adjusting the water activity of the gummy composition to be substantially closer to the water activity of the second component. Thus, in some embodiments, the gummy composition may be configured to have a water activity ($a_w1$) that is about 0.65 or less, less than about 0.62, or less than about 0.6, such as to be about 0.25 to about 0.65, about 3 to about 0.62, or about 0.4 to about 0.6. In certain embodiments, the gummy composition can have a water activity of about 0.5 to about 0.65.

Known gummy compositions based on hydrocolloid systems typically have a substantially high water activity. The water activity of the gummy composition (awl) according to the present disclosure may be lowered by altering the solids content and/or by the inclusion of humectant agents such as hydrogenated carbohydrates and/or colloidal silica. For exemplary purposes, altering the solids content of the gummy composition may be effected by cooking the gummy composition to a higher final solids content, such as at least about 78% by weight, at least about 80% by weight, or at least about 82% by weight, such as about 80% to about 85%, about 81% to about 84%, or about 80% to about 83.8% by weight, based on the total weight of the gummy composition. For further exemplary purposes, hydrogenated carbohydrates (e.g., sorbitol syrup and glycerol) can be included in a content of about 5% to about 30%, about 10% to about 25%, or about 15% to about 22% by weight based on the total weight of the gummy composition. In some embodiments, the second composition can have a water activity that is equal to or greater than the water activity of the gummy composition.

As noted above, water activities may be relative to the time of production of the respective materials since the relative water activities of the second composition and the gummy composition may tend toward equilibration over time. Accordingly, the respective water activities may be referenced to values obtained immediately following preparation of the compositions and before there is opportunity for substantial equilibration to occur. The water activities may be referenced to an average water activity for a stand-alone composition—i.e., the water activity of a gummy composition separate from a second composition core and the water activity of a second composition separate from a gummy composition shell. For exemplary purposes, following are typical water activities of exemplary materials that may be used as a second composition: 100% w/w peanut butter—$a_w$ 0.19; 40% w/w coconut fat and 60% w/w confectionary sugar—$a_w$ 0.59; 100% w/w chocolate nut paste—$a_w$ 0.20; 56% w/w glycerol and 44% w/w confectionary sugar—$a_w$ 0.06; 65% w/w glucose, 13% w/w fat, and 22% w/w condensed milk—$a_w$ 0.45; 97% w/w dark chocolate and 3% w/w palm fat—$a_w$ 0.54.

To the extent that equilibration may occur, it is preferable for the present multicomponent compositions to provide a minimum stability. For example, in one or more embodiments, a second composition utilized as a core in a center-in-shell dosage form may be prepared with an initial water activity that is less than the water activity of a gummy composition utilized as a shell around the core, and the water activity of the second composition core can remain below the water activity of the gummy composition shell for a time of about 7 days or greater, about 10 days or greater, about 14 days or greater, about 21 days or greater or about 28 days or greater, each of the foregoing being inclusive of an upper end of about 3 months, about 6 months, about 9 months, or about 1 year.

A multicomponent dosage form according to the present disclosure can have a mass in the range of about 2 g to about 6 g, about 3 g to about 5 g, or about 3.5 g to about 4 g. The dimensions of the dosage forms can vary based upon the density of the gummy composition and the second composition. Although the noted sizes are preferred, it is understood that larger (i.e., higher mass) dosage forms can be prepared if desired utilizing the materials and formulations described herein.

In one or more embodiments, the dimensions of a core composition within a gummy composition can vary relative to the dimensions of the gummy composition. In particular, it has been found that overall product characteristics can be improved by maintaining a minimum "shell" thickness. Specifically, it can be desirable for the thickness of the gummy composition shell (measured as the distance from the outer surface of the core composition to the outer surface of the gummy composition) to be about 1.5 mm or greater, about 2 mm or greater, or about 2.5 mm or greater, such as about to about 1.5 mm to about 10 mm or about 2 mm to about 8 mm. Such thickness specifically can apply to all points of the shell surrounding the core composition. The gummy shell thickness need not necessarily be constant at all points so long as the minimum shell thickness is met at all point of the gummy shell.

An oral, multicomponent dosage form can be prepared according to one or more embodiments by forming a gummy composition as described herein and forming a second composition as described herein. The two compositions can be co-deposited to form center-in-shell multicomponent dosage forms. As such, the oral, multicomponent dosage forms of the present disclosure can be defined as being a co-deposited composition. Such term can be specifically descriptive of the structure of the multicomponent dosage in that the co-deposited second composition will have a physical structure that is distinguishable from a pre-formed second composition. In the present disclosure, a co-deposited second composition will remain a liquid or set as a solid material at standard room temperatures, and such forms are expressly distinguishable from pre-formed compositions, wherein solid particles may be compressed into a unit dosage form (e.g., a tablet or caplet) or wherein a solid, pre-formed shell (e.g., hard gel capsules or soft gel capsules) is provided with or without a solid or liquid material inside the pre-formed shell. Thus, a co-deposited multicomponent dosage form as presently described has a specific, physical relationship between the gummy, outer composition and the second, inner composition. The second composition in the present disclosure thus may be defined in relation to not being a pre-formed unit (e.g., tablet, caplet, hard capsule, soft capsule, or microcapsule). The second composition in the present disclosure more particularly may be defined in relation to not being in the form of a compressed mass of solid particles or powder. In some embodiments, the second composition can be defined in relation to being in direct contact with the gummy composition—i.e., the second composition in the multicomponent dosage form is not separated from the gummy composition by an intervening layer. The term "co-deposited" is understood to mean that the gummy composition and the second composition are simultaneously deposited into a mold to achieve their respective final forms. A gummy composition and a second composition that are co-deposited are both in a condition for processing through suitable machinery (e.g., an extrusion apparatus) at the time of co-deposition. Both the gummy composition and the second composition may be in the form of a viscous fluid at the time of co-deposition.

Two separate hoppers can be used in the co-deposition process, one to hold the flowable gummy composition and one to hold the second composition, which is used as the center filling. The two compositions thus can be held at different temperatures if necessary. For example, the gummy composition preferably is maintained at a temperature of about 95° C. or greater to prevent premature gelling of the composition. On the other hand, it can be useful to maintain embodiments of the second composition at a temperature that is lower than the temperature of the gummy composition but still within the processing temperature range of the second composition wherein it is a viscous fluid. For example, it may be useful to keep chocolate based compositions at a temperature of less than 60° C. The hoppers may be insulated to maintain the respective temperatures necessary for the separate compositions.

Preferably, the gummy composition and the second composition can be adapted to have substantially matched densities. Matched densities can mean that the density of the two compositions differs by no more than 50%, no more than 25%, or no more than 10%. Likewise, the gummy composition and the second composition can be adapted to have substantially matched viscosities. Matched viscosities can mean that the viscosity of the two compositions differs by no more than 50%, no more than 25%, or no more than 10%.

A manifold can be used to bring the two compositions together. In the manifold, the gummy composition can be extruded in an outer annulus while the second composition is extruded through an inner port such that the gummy composition is deposited around the second composition. The temperatures of the compositions can drop significantly at this point so that the gummy composition rapidly gels so that the second (center) composition is enclosed.

Processing of the gummy composition and the second composition to form the multicomponent dosage form as described herein can be dependent, in some embodiments, upon the viscosities of the compositions, particularly the viscosity of the second composition when in the form of a viscous fluid. As used herein, a "viscous fluid" is understood to mean a physical form wherein the composition exhibits fluid properties in that it does not have a fixed shape and will yield to application of a force to be flowable, particularly upon addition of heat. The viscous fluid will have a viscosity that is greater than water under the same conditions, particularly at least two times, at least five times, or at least ten times the viscosity of water under the same conditions. As described above, the second component can be a viscous fluid at a temperature of about 40° C. to about 100° C. A viscous fluid thus can be defined in relation to its viscosity at a temperature within such range. For example, at a temperature of approximately 50° C., a viscous fluid may be a fluid having a viscosity of about 0.01 PaS to about 30 PaS, about 0.1 PaS to about 20 PaS, or about 0.2 PaS to about 10 PaS. As a particular example, at a temperature of approximately 50° C., a viscous fluid may be a fluid having a viscosity of about 0.3 PaS to about 8.6 PaS.

In some embodiments, a viscous fluid can particularly be a non-newtonian fluid. The viscosity thus may be particularly defined in relation to the shear rate at which the viscosity is measured. For example, a viscous fluid useful according to the present disclosure can exhibit a viscosity as defined above as measured across a shear rate of 3.5 $s^{-1}$ to 982 $s^{-1}$.

Viscous fluids as described herein can be particularly configured for co-extrusion with the gummy composition. For example, co-deposition may be carried out using commercial manufacturing equipment, such as the Baker Perkins Servoform™ Jelly Depositor or the Winkler and Dunnebier 462 Depositor. As in the case of the Baker Perkins apparatus, a separate pump system can be used for each component with a spring-loaded ball valve between the pump sections and the depositor nozzle. The pumps for the depositors can be located within the storage hoppers of the machine, and constant volume piston in cylinder pumps can be used. In the case of the Winkler and Dunnebier apparatus, a mechanically operated rotary valve can be positioned between the pump system (which can be substantially similar to the system as described above) and the depositor nozzle. The depositing volume (and thus the net weight) is adjustable for both the gummy composition and the second composition (e.g., the core composition). As a non-limiting example, the total depositing weight can be maintained at about 3.5 g with a 20% w/w fill of the core composition. A suitable depositing rate can be approximately 40 to 60 deposits per minute with the core deposit taking between 0.8 seconds and 1 second.

Viscosity values for the viscous liquid can be measured using known methods. For example, TABLE 1 and TABLE 2 provide measured viscosity values for a second composition within the scope of the present disclosure. The inventive second composition was tested with a TA Instruments AR500 rheometer using a DIN standard concentric cylinder system wherein the inner cylinder had a conical end. The radii of the inner and outer cylinders were 14 mm and 15 mm, respectively, and the inner cylinder had a height of 42 mm. After loading, the sample was allowed to rest for 10 minutes to attain thermal equilibrium at a temperature of 50° C. Shear stress and viscosity measurements were made with a series of fixed shear rates between 1.452 $s^{-1}$ and 1452 $s^{-1}$. The shear rate steps were equally spaced logarithmically with 5 steps per decade of shear rate. Viscosity was calculated by dividing shear stress by shear rate. Compositions with viscosities within the above-defined ranges, as confirmed by the testing values shown in TABLE 1 and TABLE 2, were found to be particularly suitable for enabling co-deposition of the second composition with a gummy composition (which typically is deposited at a higher temperature than the second composition). As such, in some embodiments, a second component can be considered to be viscous fluid per the present disclosure when the composition has a viscosity within the defined ranges noted above when at a temperature of about 50° C.

TABLE 1

| Shear Rate $S^{-1}$ | Viscosity PaS | Shear Stress Pa |
| --- | --- | --- |
| 3.7 | 2.5 | 9.6 |
| 61.96 | 0.8 | 48.8 |
| 982 | 0.3 | 337.8 |

TABLE 2

| Shear Rate $S^{-1}$ | Viscosity PaS | Shear Stress Pa |
| --- | --- | --- |
| 3.7 | 8.6 | 31.1 |
| 61.96 | 2.45 | 142.8 |
| 982 | 0.64 | 599.8 |

Although the viscosities described above are calculated through measurements of shear rate and shear stress, it is understood that substantially similar viscosities would be obtained utilizing different measurement techniques and equipment. Thus, the viscosity of the second composition is not expected to differ based upon the measurement technique and/or equipment utilized.

Embodiments of the present disclosure are further illustrated by the following examples, which are set forth to illustrate the presently disclosed subject matter and are not to be construed as limiting. Various examples relate to compositions that include chocolate materials. In relation to such examples, it is understood that white and dark chocolate used generally contain 25% to 35% w/w fat together with permitted emulsifiers. In addition to cocoa butter and milk fat, formulations may contain up to 5% w/w of vegetable fats depending on local regulatory requirements. Dark chocolate typically contains 35% to 60% w/w sugar and 65% to 35% w/w cocoa solids (some of which is cocoa butter) and 10% to 30% w/w non-fat cocoa solids. White chocolate typically contains 35% to 55% w/w sugar and 20% to 35% w/w milk solids. The only cocoa solids present in white chocolate will be in the form of cocoa fat. The particle size of chocolates is typically <28 microns but may be significantly finer.

Example 1—Gummy Composition

A gummy composition was prepared using the components shown in TABLE 3. A first solution was formed by combining the gelatin, sucrose, and water at 60° C. A second solution was formed by combining the glucose syrups and sucrose and warming to 60° C. The first and second solutions were combined, and the calcium carbonate was added with mixing. The blended mixture (slurry) was held at 55-60° C. in a batch tank. The slurry was heated to 104° C. and flash cooled to 90° C. reduce solids to 82/84 Brix. Thereafter, natural flavors and colors were added along with citric acid to form the gel.

TABLE 3

| Hydrocolloid Matrix Component | Amount (% w/w) |
| --- | --- |
| Gelatin 250 bloom | 5.89 |
| Pectin CS502 | 0.15 |

TABLE 3-continued

| Hydrocolloid Matrix Component | Amount (% w/w) |
|---|---|
| Sucrose | 2.46 |
| Water (60° C.) | 15.17 |
| Glucose Syrup 63 DE | 28.00 |
| Glucose Syrup 43 DE | 15.00 |
| Sucrose | 25.54 |
| Calcium carbonate | 6.70 |
| Color/Flavoar | 1.04 |
| Citric Acid | 0.05 |

Example 2—Gummy Composition

A gummy composition was prepared using the components shown in TABLE 4. The pectin and carragennan were mixed with the dispersing sucrose and hydrated in the water at 80° C. Separately, the glucoses were heated in the dispersing water to 90° C. The sucrose was added to the glucose/water mixture and heated to 90-100° C. The pectin/carragennan mixture was added to the glucose mixture to form a slurry. The slurry was heated to 104° C. and flash cooled to 90° C. reduce solids to 82/84 Brix Thereafter, natural flavors and colors were added along with citric acid to form the gel.

TABLE 4

| Hydrocolloid Matrix Component | Amount (% w/w) |
|---|---|
| Pectin CS502 | 2.00 |
| Carrageenan 310C | 0.50 |
| Sucrose (to disperse) | 3.00 |
| Water | 20.00 |
| Water (to disperse) | 4.50* |
| Glucose 42 | 16.00 |
| Glucose 63 | 29.00 |
| Sucrose | 24.00 |
| Flavor Color/Acid | 5.50 |

*Remove during processing

Example 3—Gummy Composition

A gummy composition was prepared using the components shown in TABLE 5. The pectin was dissolved in water, the glucose was heated to 80° C. in a mixing vessel, and the pectin solution was added to the warmed glucose. The sucrose was added, and the mixture was heated to 90-100° C. Once all sugar was dissolved, the mixture was transferred to a feed tank and cooked until the desired solids content was achieved. Thereafter, the citric acid was added to form the gel.

TABLE 5

| Hydrocolloid Matrix Component | Amount (% w/w) |
|---|---|
| Pectin CS502 | 2.3 |
| Water | 12.9 |
| Glucose syrup solids | 56.0 |
| Sucrose | 28.8 |
| Citric acid | 1.0 |

Example 4—Gummy Composition

A gummy composition was prepared using the components shown in TABLE 6. The pectin was blended with the dispersing sucrose and hydrated in water at 80° C. with mixing. The glucose was heated to 80° C. in a mixing vessel, and the pectin solution was added to the warmed glucose. The sucrose was added, and the mixture was heated to 90-100° C. Once all sugars were dissolved, the mixture was cooked to a solids content of 80/82 Brix. Thereafter, citric acid, malic acid, and flavors were added to form the gel.

TABLE 6

| Hydrocolloid Matrix Component | Amount (% w/w) |
|---|---|
| Pectin CS502 | 2.3 |
| Sucrose (to disperse) | 3.5 |
| Water | 12.9 |
| Glucose syrup solids | 56.0 |
| Sucrose | 25.3 |
| Citric acid | 0.5 |
| Malic acid | 0.5 |
| Flavors | 0.7 |

Example 5—Lipophilic Composition

A lipophilic composition suitable for use as the second composition in a multicomponent dosage form was prepared using the components shown in TABLE 7. The peanut butter was combined with the fat and warmed to 60° C., and the confectionary sugar was blended in to the warmed mixture to form a flowable composition.

TABLE 7

| Lipophilic Composition Component | Amount (% w/w) |
|---|---|
| Peanut butter | 70.0 |
| AAK Fat | 10.0 |
| Confectionary sugar | 20.0 |

Example 6—Lipophilic Composition

A lipophilic composition suitable for use as the second composition in a multicomponent dosage form was prepared using the components shown in TABLE 8. The coconut fat was warmed to 60° C. The confectionary sugar was blended with the active agents (folic acid, calcium d-pantothenate, and ascorbic acid), and combination was dispersed in the heated fat to form a flowable composition.

TABLE 8

| Lipophilic Composition Component | Amount (% w/w) |
|---|---|
| Coconut fat | 40.0 |
| Confectionary sugar | 54.27 |
| Folic acid | 0.5 |
| Calcium d-pantothenate | 1.44 |
| Ascorbic acid | 3.79 |

Example 7—Lipophilic Composition

A lipophilic composition suitable for use as the second composition in a multicomponent dosage form was prepared using the components shown in TABLE 9. The NUTELLA® was combined with the fat and warmed to 60° C., and the confectionary sugar was blended in to the warmed mixture to form a flowable composition.

TABLE 9

| Lipophilic Composition Component | Amount (% w/w) |
| --- | --- |
| NUTELLA ® | 70.0 |
| AAK Fat | 10.0 |
| Confectionary sugar | 10.0 |

Example 8—Lipophilic Composition

A lipophilic composition suitable for use as the second composition in a multicomponent dosage form was prepared using the components shown in TABLE 10. The white chocolate was mixed with the fat and warmed to 60° C. The active agents (folic acid, calcium d-pantothenate, and ascorbic acid) were pre-blended and then dispersed in the heated chocolate to form a flowable composition

TABLE 10

| Lipophilic Composition Component | Amount (% w/w) |
| --- | --- |
| White chocolate | 90.27 |
| AAK Fat | 4.0 |
| Folic acid | 0.5 |
| Calcium d-pantothenate | 1.44 |
| Ascorbic acid | 3.79 |

Example 9—Lipophilic Composition

A lipophilic composition suitable for use as the second composition in a multicomponent dosage form was prepared using the components shown in TABLE 11. The white chocolate was mixed with the fat and warmed to 50° C. to form a flowable composition.

TABLE 11

| Lipophilic Composition Component | Amount (% w/w) |
| --- | --- |
| White chocolate | 95.5 |
| AAK Fat | 4.5 |

Example 10—Lipohilic Composition

A lipophilic composition suitable for use as the second composition in a multicomponent dosage form was prepared using the components shown in TABLE 12. The coconut fat was warmed to 60° C. The active agents (multivitamin blend and tricalcium phosphate) were pre-blended and then dispersed in the heated fat followed by addition of the color and flavor to form a flowable composition.

TABLE 12

| Lipophilic Composition Component | Amount (% w/w) |
| --- | --- |
| Coconut fat | 56.03 |
| Multivitamin blend | 19.96 |
| Tricalcium phosphate | 23.12 |
| Color | 0.15 |
| Flavor | 0.70 |

Example 11—Lipophilic Composition

A lipophilic composition suitable for use as the second composition in a multicomponent dosage form was prepared using the components shown in TABLE 13. The coconut fat was warmed to 60° C., and the confectionary sugar was dispersed in the heated coconut fat to form a flowable composition.

TABLE 13

| Lipophilic Composition Component | Amount (% w/w) |
| --- | --- |
| Coconut fat | 42.1 |
| Confectionary sugar | 57.9 |

Example 12—Lipophilic Composition

A lipophilic composition suitable for use as the second composition in a multicomponent dosage form was prepared using the components shown in TABLE 14. The coconut fat was warmed to 60° C. The vitamin pre-mix was dispersed with the confectionary sugar in the heated coconut fat to form a flowable composition.

TABLE 14

| Lipophilic Composition Component | Amount (% w/w) |
| --- | --- |
| Coconut fat | 37.0 |
| Confectionary sugar | 32.35 |
| Vitamin pre-mix | 30.65 |

Example 13—Lipophilic Composition

A lipophilic composition suitable for use as the second composition in a multicomponent dosage form was prepared using the components shown in TABLE 15. The dark chocolate was mixed with the palm fat and warmed to 50° C. to form a flowable composition.

TABLE 15

| Lipophilic Composition Component | Amount (% w/w) |
| --- | --- |
| Dark chocolate | 96.0 |
| Palm Fat | 4.0 |

Example 14—Lipophilic Composition

A lipophilic composition suitable for use as the second composition in a multicomponent dosage form was prepared using the components shown in TABLE 16. The peanut butter was combined with the palm fat and warmed to 60° C., and the confectionary sugar was blended in to the warmed mixture to form a flowable composition.

TABLE 16

| Lipophilic Composition Component | Amount (% w/w) |
| --- | --- |
| Peanut butter | 70.0 |
| Palm Fat | 10.0 |
| Confectionary sugar | 20.0 |

Example 15—Hydrophilic Composition

A hydrophilic composition suitable for use as the second composition in a multicomponent dosage form was prepared using the components shown in TABLE 17. The glycerol was warmed to 60° C., and the colors and flavors were added thereto. The active agents (folic acid, calcium d-pantothenate, and ascorbic acid) were pre-blended and then dispersed with the confectionary sugar in the heated glycerol to form a flowable composition.

TABLE 17

| Hydrophilic Composition Component | Amount (% w/w) |
|---|---|
| Glycerol | 54.0 |
| Confectionary sugar | 43.88 |
| Colors | 0.2 |
| Flavors | 1.0 |
| Folic acid | 0.5 |
| Calcium d-pantothenate | 1.15 |
| Ascorbic acid | 3.79 |

Example 16—Hydrophilic Composition

A hydrophilic composition suitable for use as the second composition in a multicomponent dosage form was prepared using the components shown in TABLE 18. The glycerol was warmed to 50° C., and the colors and flavors were added thereto. The confectionary sugar was then dispersed in the heated glycerol to form a flowable composition.

TABLE 18

| Hydrophilic Composition Component | Amount (% w/w) |
|---|---|
| Glycerol | 54.5 |
| Confectionary sugar | 44.29 |
| Colors | 0.2 |
| Flavors | 1.01 |

Example 17—Hydrophilic Composition

A hydrophilic composition suitable for use as the second composition in a multicomponent dosage form was prepared using the components shown in TABLE 19. The glycerol was warmed to 50° C., and the vitamin pre-mix with the confectionary sugar was dispersed in the heated glycerol to form a flowable composition.

TABLE 19

| Hydrophilic Composition Component | Amount (% w/w) |
|---|---|
| Glycerol | 30.0 |
| Confectionary sugar | 39.35 |
| Vitamin pre-mix | 30.65 |

Example 18—Hydrophilic Composition

A hydrophilic composition suitable for use as the second composition in a multicomponent dosage form was prepared using the components shown in TABLE 20. The glycerol was warmed to 50° C., and the color and flavor were added thereto. The confectionary sugar was then dispersed in the heated glycerol to form a flowable composition.

TABLE 20

| Hydrophilic Composition Component | Amount (% w/w) |
|---|---|
| Glycerol | 54.0 |
| Confectionary sugar | 45.5 |
| Color | 0.3 |
| Flavor | 0.2 |

Example 19—Hydrophilic Composition

A hydrophilic composition suitable for use as the second composition in a multicomponent dosage form was prepared using the components shown in TABLE 21. The LYCASIN® syrups were boiled to a solids content of 85 Brix then cooled to 50° C. Thereafter, the color and flavor were added to form a flowable composition.

TABLE 21

| Hydrophilic Composition Component | Amount (% w/w) |
|---|---|
| LYCASIN ® 75/75 (75% maltitol) | 65.0 |
| LYCASIN ® HBC (55% maltitol) | 35.0 |
| Color | 0.5 |
| Flavor | 0.5 |

Example 20—Preparation of Oral, Chewable Dosage Form

A gummy (shell) formulation was produced by hydrating dried pectin with water and then combining this with a mixture of sugar and glucose syrup heated to about 80° C. This mix was then heated to drive off moisture until a solids content of 79%-84% was reached, at which point color, flavor, and acid were added, and a temperature of 100° C. was maintained. The acid adjusted the pH to approximately 3.5. Once the pH was adjusted, the gummy formulation was in a condition to set rapidly below a temperature of about 95° C.

A core formulation was produced by melting a suitable fat at about 50° C. and adding to that a bulking agent, vitamin mix, color and flavor before mixing thoroughly to achieve a homogeneous mix maintained at 50° C.

The gummy formulation was transferred to one of the two hoppers of the depositing machine and the core formulation was transferred to the second hopper of the same machine. The hoppers were maintained at the appropriate temperature for the contents. The depositing machine then co-deposited the two components into molds by a carefully timed and controlled deposit such that the shell completely enveloped the core. The molds may be metal, plastic, rubber, or formed in starch powder. For metal, plastic, or rubber molds, it is normal to apply a release agent. After depositing, the molds and contents were cooled as rapidly as possible using a flow of cold air. Once the units were cooled to around 20° C. they were removed from the molds and were in condition for applying any desired post-molding treatment.

Example 21—Effect of Increased Solids Content on Water Activity

The effect of increased solids content on the water activity of a gummy composition was evaluated by preparing a gummy composition and cooking the gummy composition to gradually increase the solids content with periodic water activity measurements. The gummy composition comprised:

pectin (1.9%), sucrose (31.75%), glucose 42DE solids (31.75%), glycerol (17.64%), citric acid solids (0.44%), all values being w/w. Solids content and corresponding water activity are shown in TABLE 22 below.

TABLE 22

| Solids content (%) | Water activity ($A_w 1$) |
|---|---|
| 79 | 0.709 |
| 80 | 0.655 |
| 81 | 0.651 |
| 82 | 0.623 |
| 84 | 0.614 |

Example 22—Effect of Added Humectant on Water Activity

The effect of adding a polyol humectant (sorbitol syrup and glycerol) on the water activity of gummy compositions cooked to the same solids content (84%) was evaluated. The respective compositions and the associated water activities are shown in TABLE 23 through TABLE 25 below.

TABLE 23

| Raw ingredients | Percentage (%) in gummy composition | Water activity ($A_w 1$) of gummy composition |
|---|---|---|
| Pectin | 1.91 | 0.614 |
| Sucrose | 31.75 | |
| Glucose 42DE solids | 49.40 | |
| Citric acid solids | 0.44 | |
| Water | 16.50 | |

TABLE 24

| Raw ingredients | Percentage (%) in gummy composition | Water activity ($A_w 1$) of gummy composition |
|---|---|---|
| Pectin | 1.80 | 0.539 |
| Sucrose | 28.36 | |
| Glucose 42DE solids | 36.00 | |
| Sorbitol syrup | 20.00 | |
| Citric acid solids | 0.44 | |
| Water | 13.40 | |

TABLE 25

| Raw ingredients | Percentage (%) in gummy composition | Water activity ($A_w 1$) of gummy composition |
|---|---|---|
| Pectin | 1.80 | 0.387 |
| Sucrose | 28.36 | |
| Glucose 42DE solids | 36.00 | |
| Glycerol | 16.00 | |
| Citric acid solids | 0.44 | |
| Water | 17.40 | |

Example 23—Effect of Added Humectant on Water Activity

The effect of added polyol humectants (sorbitol, mannitol, glycerol), mono-saccharide (fructose), and guar gum on the water activity of gummy compositions cooked to the same solids content (80%) was evaluated. Compositions and results are shown in TABLE 26.

TABLE 26

| | Shell Variants | | | | | |
|---|---|---|---|---|---|---|
| Ingredients | Control wt % | v1 wt % | v2 wt % | v3 wt % | v4 wt % | v5 wt % |
| Pectin CS 502 | 2.3 | 2.3 | 2.3 | 2.3 | 2.3 | 2.3 |
| Sucrose (to disperse) | 3.5 | 3.5 | 3.5 | 3.5 | 3.5 | 3.5 |
| Water | 12.9 | 12.9 | 12.9 | 12.9 | 12.9 | 12.9 |
| Glucose 42 | 56 | 46 | 46 | 46 | 56 | 46 |
| Sucrose | 25.3 | 25.3 | 25.3 | 25.3 | 15.3 | 25.3 |
| Sorbitol | — | 10 | — | — | — | — |
| Mannitol | — | — | 10 | — | — | — |
| Glycerol | — | — | — | 10 | — | — |
| Fructose | — | — | — | — | 10 | — |
| Guar Gum | — | — | — | — | — | 10 |
| Total % Composition | 100% | 100% | 100% | 100% | 100% | 100% |
| Citric acid (50% w/w) | 1 | 1 | 1 | 1 | 1 | 1 |
| Gummy Initial $a_w$ | 0.68 | 0.5119 | 0.5698 | 0.4272 | 0.5829 | 0.5570 |

Many modifications and other embodiments of the inventions set forth herein will come to mind to one skilled in the art to which these inventions pertain having the benefit of the teachings presented in the foregoing descriptions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A chewable, multicomponent composition for oral administration, the multicomponent composition comprising:
    a first component that is a hydrocolloid system comprising 70% to about 94% w/w of one or more hydrophilic bulking agents, about 1% to about 20% w/w of one or more hydrophilic, long-chain polymers, and about 5% to about 35% w/w of a water source, the first component being in the form of a gel;
    a second component comprising a lipidic base in an amount of about 20% to about 70% by weight of the second component and one or more hydrophilic bulking agents in an amount of about 10% to about 70% by weight of the second component, the lipidic base having a melting temperature of about 10° C. to about 50° C., wherein the second component is solid at a temperature of about 35° C. or less and is a viscous fluid at a temperature of about 40° C. to about 100° C.; and
    an active ingredient;
    wherein the second component is at least partially surrounded by the first component.

2. The multicomponent composition of claim 1, wherein the composition is in a core/shell conformation with the first component forming a shell surrounding at least one core formed of the second component.

3. The multicomponent composition of claim 2, wherein the first component has a thickness, measured as the distance between an outer surface of the at least one core, and an outer surface of the first component, of about 1 mm or greater at all points.

4. The multicomponent composition of claim 1, wherein one or more of the following conditions is met:
the active ingredient is included in the second component;
the active ingredient is included in the first component;
a plurality of active ingredients are included;
the active ingredient is in an encapsulated form;
the hydrocolloid system of the first component is elastic or viscoelastic;
the hydrocolloid system has a solids content of at least about 78% by weight.

5. The multicomponent composition of claim 1, wherein the active ingredient is a natural or synthetic substance that is recognized as being beneficial to human health and is selected from the group consisting of non-steroidal anti-inflammatory drugs (NSAIDs), analgesics, antihistamines, decongestants, antitussives, expectorants, sleep aids, antibiotics, laxatives, anti-diarrheals, anthelmintics, antacids, vitamins, minerals, phytonutrients, fiber, fatty acids, amino acids, polypeptides, botanicals, herbs, prebiotics, probiotics, and combinations thereof.

6. The multicomponent composition of claim 1, wherein one or more of the following conditions is met:
the one or more hydrophilic bulking agents of the first component includes one or more saccharides or saccharide derivatives;
the one or more hydrophilic bulking agents of the first component includes one or more hydrogenated carbohydrates;
the one or more hydrophilic bulking agents of the first component includes one or both of sugar solids and granulated sugar;
the one or more hydrophilic bulking agents of the first component includes glucose, sucrose, and sorbitol.

7. The multicomponent composition of claim 1, wherein the second component, in the form of a viscous fluid, has a viscosity of about 0.01 to about 30 PaS at a temperature of about 50° C.

8. The multicomponent composition of claim 1, wherein the hydrophilic bulking agent and the lipidic base in the second component are present in a ratio of about 0.2 to about 0.8.

9. The multicomponent composition of claim 1, wherein the hydrophilic bulking agent in the second component comprises a material selected from the group consisting of saccharides, saccharide derivatives, hydrogenated carbohydrates, emulsifiers, proteins, processing aids, inorganic salts, active ingredients, and combinations thereof.

10. The multicomponent composition of claim 9, wherein one or both of the following conditions is met:
the hydrophilic bulking agent in the second component is selected from the group consisting of sucrose, glucose, dextrose, maltose, variations thereof, and combinations thereof;
the hydrophilic bulking agent in the second component is selected from the group consisting of sorbitol, glycerol, mannitol, maltitol, erythritol, lactitol, isomalt, and combinations thereof.

11. The multicomponent composition of claim 1, wherein the first component is a hydrocolloid system comprising about 70% to about 94% w/w of one or more saccharides or saccharide derivatives, about 1% to about 15% w/w of one or more hydrophilic, long-chain polymers comprising at least pectin, and about 10% to about 25% w/w of a water source, the first component being in the form of a gel.

12. The multicomponent composition of claim 1, wherein the first component is one or both of: configured to be reduced to smaller pieces through mastication; and configured to dissolve within the mouth.

13. The multicomponent composition of claim 1, wherein the first component has a water activity $a_w1$, the second component has a water activity $a_w2$, and $a_w1$ is greater than $a_w2$ prior to combining the first component and the second component.

14. The multicomponent composition of claim 13, wherein $a_w1$ is greater than $a_w2$ by at least 0.05.

15. The multicomponent composition of claim 14, wherein one of the following conditions is met:
$a_w1$ is about 0.65 or greater;
$a_w1$ is about 0.5 to about 0.65.

16. The multicomponent composition of claim 1, wherein the lipidic base is a fat from one or more of a vegetable source, an animal source, a nut source, and a seed source.

17. The multicomponent composition of claim 1, wherein the lipidic base is a fat from one or more of cocoa, palm, and coconut.

* * * * *